(12) United States Patent
McLaughlin et al.

(10) Patent No.: US 9,296,120 B2
(45) Date of Patent: Mar. 29, 2016

(54) METHOD OF PRODUCING DRAFTS OF SLICED FOOD PRODUCTS WITH DESIRED WEIGHTS AND A DUAL SCALE WEIGHING SYSTEM FOR PRODUCING DRAFTS OF DESIRED WEIGHTS

(76) Inventors: Paul McLaughlin, South Chicago Heights, IL (US); Brad DeBlecourt, Lockport, IL (US); Thomas C. Wolcott, La Grange, IL (US); Scott A. Lindee, Mokena, IL (US)

(*) Notice: Subject to any disclaimer, the term of this patent is extended or adjusted under 35 U.S.C. 154(b) by 422 days.

(21) Appl. No.: 13/504,024
(22) PCT Filed: Oct. 26, 2010
(86) PCT No.: PCT/US2010/054155
§ 371 (c)(1),
(2), (4) Date: Apr. 25, 2012
(87) PCT Pub. No.: WO2011/056602
PCT Pub. Date: May 12, 2011

(65) Prior Publication Data
US 2012/0205164 A1 Aug. 16, 2012

Related U.S. Application Data

(60) Provisional application No. 61/255,091, filed on Oct. 26, 2009, provisional application No. 61/255,442, filed on Oct. 27, 2009.

(51) Int. Cl.
*B26D 7/30* (2006.01)
*G01G 13/02* (2006.01)
(Continued)

(52) U.S. Cl.
CPC .. *B26D 7/30* (2013.01); *B26D 5/00* (2013.01); *G01G 15/02* (2013.01); *G01G 17/02* (2013.01); *G01G 19/306* (2013.01); *G01G 19/56* (2013.01); *B26D 2210/02* (2013.01); *G01G 21/30* (2013.01)

(58) Field of Classification Search
CPC .............. B26D 5/00; B26D 5/20; B26D 7/30;
B26D 7/32; B26D 2210/02; G01G 13/00;
G01G 13/02; G01G 13/04; G01G 17/00;
G01G 17/02; G01G 19/306; G01G 19/382;
G01G 19/414; G01G 19/52; G01G 19/56
USPC .................. 83/77; 53/502; 177/25.13, 52, 125
See application file for complete search history.

(56) References Cited

U.S. PATENT DOCUMENTS 3,099,304 A 7/1963 Monsees
3,605,837 A 9/1971 Lambert et al.
(Continued)

FOREIGN PATENT DOCUMENTS

DE 3617336 A1 11/1987
DE 3703807 A1 8/1988
GB 2173008 A 10/1986

OTHER PUBLICATIONS

European Search Report and Written Opinion for EP 10 82 8863 dated Jul. 17, 2014, 9 pages.
(Continued)

*Primary Examiner* — Randy W Gibson
(74) *Attorney, Agent, or Firm* — Klintworth & Rozenblat IP LLC

(57) ABSTRACT

A method for weighing sliced products to generate product batches of a pre-determined weight. A slicer slices products which are disposed onto a slice scale located beneath the output end of the slicer. An intermediate weight is measured at a pre-determined point in the slicing process. The intermediate weight information is used to calculate the minimum number of completion slices, based on thicknesses of the slices, needed to meet the target weight. The competed draft is transferred to a check sale where a final draft weight is measured and compared to a sum of the intermediate weight and the weight of the completion slices. Comparison of the weight is used to adjust slicing parameters for more precise targeting of the desired weight of the next draft. Completion slices may be adjusted in thickness to minimize the giveaway weight.

11 Claims, 4 Drawing Sheets

(51) Int. Cl.
*G01G 19/34* (2006.01)
*G01G 19/56* (2006.01)
*G01G 19/30* (2006.01)
*B26D 5/00* (2006.01)
*G01G 15/02* (2006.01)
*G01G 17/02* (2006.01)
*G01G 21/30* (2006.01)

(56) References Cited

U.S. PATENT DOCUMENTS

| | | | |
|---|---|---|---|
| 3,667,520 A | 6/1972 | Flesch | |
| 3,827,319 A | 8/1974 | Flesch | |
| 3,835,742 A | 9/1974 | Spooner | |
| 3,846,957 A | 11/1974 | Divan | |
| 3,846,958 A * | 11/1974 | Divan | 53/502 |
| 3,905,259 A | 9/1975 | Spooner et al. | |
| 3,906,823 A | 9/1975 | Spooner et al. | |
| 3,954,166 A * | 5/1976 | Ives et al. | 53/502 |
| 4,065,911 A * | 1/1978 | Fagan | 53/53 |
| 4,545,447 A | 10/1985 | Spooner | |
| 4,548,108 A * | 10/1985 | Dennis | 83/27 |
| 4,580,475 A | 4/1986 | Antonissen | |
| 4,720,961 A * | 1/1988 | Jordan | 53/502 |
| 4,794,996 A * | 1/1989 | Wallace et al. | 177/25.14 |
| 5,109,936 A | 5/1992 | Ruppel | |
| 5,499,719 A * | 3/1996 | Lindee et al. | 209/703 |
| 5,566,600 A * | 10/1996 | Johnson et al. | 83/77 |
| 5,937,080 A | 8/1999 | Vogeley, Jr. et al. | |
| 5,974,925 A * | 11/1999 | Lindee et al. | 83/412 |
| 6,320,141 B1 * | 11/2001 | Lindee et al. | 177/25.13 |
| 6,640,681 B1 | 11/2003 | Weber | |
| 6,731,094 B1 | 5/2004 | Itoh et al. | |
| 7,279,644 B1 * | 10/2007 | Kasel | 177/25.13 |
| 7,411,137 B2 | 8/2008 | Sandberg et al. | |
| 8,759,694 B2 * | 6/2014 | Weber | 177/52 |
| 2002/0184983 A1 * | 12/2002 | Lau et al. | 83/77 |
| 2003/0145700 A1 * | 8/2003 | Lindee | 83/29 |
| 2008/0283306 A1 | 11/2008 | Grove | |
| 2011/0232445 A1 * | 9/2011 | Weber | 83/77 |
| 2012/0031682 A1 * | 2/2012 | Weber | 177/52 |

OTHER PUBLICATIONS

Notification of Transmittal of International Search Report & Written Opinion dated Jan. 26, 2011.

* cited by examiner

METHOD OF PRODUCING DRAFTS OF SLICED FOOD PRODUCTS WITH DESIRED WEIGHTS AND A DUAL SCALE WEIGHING SYSTEM FOR PRODUCING DRAFTS OF DESIRED WEIGHTS

This application is a nationalization of PCT application PCT/US2010/054155 filed on Oct. 26, 2010, and claims the benefit of U.S. Provisional Patent Application 61/255,091 filed Oct. 26, 2009 and U.S. Provisional Patent Application 61/255,442 filed Oct. 27, 2009.

FIELD OF THE INVENTION

This invention relates in general to slicing systems and methods of weighing sliced food products.

BACKGROUND OF THE INVENTION

Food of various kinds, including sliced deli meats, sausage, cheese and bacon, are frequently sliced in high volume automated slicing machines, wherein the food products are cut into slices and transported in portions for further processing, such as weighing and packaging. Slicing machines such as the one disclosed in U.S. Pat. No. 4,548,108, and other machines capable of continuous high volume output, can be used.

Food industry regulation of labeling practices requires precise weight measurements of food corresponding to the package label. To ensure that consumers receive packaged goods reflecting the weight shown on the label, it is necessary to weigh the food product carefully before packaging. However, the process of weighing sliced food product can be time consuming, and calculating the additional slices needed to reach the desired weight limits the efficiency of the manufacturing process.

In many cases, food manufacturers err on the side of caution and end up packing more, by weight, of the food product so as not to fall short of the weight requirement. This additional weight is referred to as the give-away weight. Processing food slices so as to minimize the give-away weight poses numerous challenges, due to the often irregular shape of various food types. Food types, especially meats, can be irregularly shaped, and can have progressive variations in density, unexpected changes in composition, or changes in other parameters, sometimes as a result of temperature dependent conditions.

U.S. Pat. Nos. 3,099,304; 3,667,520; 4,065,911; and 4,545,447 disclose methods and apparatus for stacking and weighing slices of cut food products. U.S. Pat. No. 6,640,681 relates to a method and a device that allows portions of similar slices to be obtained even if the product that is sliced is changed.

U.S. Pat. No. 3,099,304 discloses an apparatus for stacking and weighing sliced food products, and controlling the weight of the stacks produced. The apparatus is initially set to receive a certain number of slices. The slices are deposited on a stacker turret which rotates when a certain period of time has elapsed and a given number of slices have been deposited. Stacks are transferred to a conveyer mounted on a stack to check-weigh the stack. The apparatus uses a feed-back control mechanism for the check-weigher to the feed control of the slicing machine in order to vary the speed of the feed mechanism when the stack of slices is overweight or underweight.

U.S Pat. No. 3,667,520 discloses a slicer control system comprising a weight monitoring system for comparing the weight of the slices cut against a predetermined standard. The weight monitoring system prematurely actuates a take-away conveyor when a predetermined error exists even though the predetermined ecmber of slices has not yet been cut, in order to minimize the number of groups of slices having gross errors that would result in rejection for weight deviations from the standard.

U.S. Pat. No. 4,065,911 discloses a combination bacon slicing, segregating and weighing apparatus which is designed to interrupt the feeding mechanism when slices are at a weight less than prescribed. The apparatus provides for weighing, counting and registering the weight of the light weight group, and calculates a new feed rate which will produce a number of whole slices at the right thickness in making up the added weight to produce the draft target weight.

U.S. Pat. No. 4,545,447 provides an apparatus for stacking and weighing slices of cold cuts. A scale is positioned with respect to the stacker to register the weight after a preselected amount of slices are collected on the stacker.

The present inventors have recognized that known prior art slicing and weighing apparatus and methods described, and others, have been disadvantageous for various reasons. The additional step of weighing the sliced food product is often time consuming and may require stopping the slicer or stopping the conveyor belts. Furthermore, the step of determining the additional amount of product needed to meet the target weight, and completing the slices, is also time consuming. There is a need to increase the economic efficiency of slicing and weighing sliced food products. The method and apparatus of the present invention allows for more efficient slicing and weighing of the food product, and provides a calibration of processing parameters after each weighing of the final draft product to ensure fine tuned accuracy of each following draft.

SUMMARY OF THE INVENTION

The present invention provides a method and apparatus for producing stacks of food slices of precise weights.

The present invention provides a method and apparatus for fine-tuning the weighing of subsequent drafts.

In one aspect, the slicing apparatus comprises dual scales--a slice scale and a check scale. The slice scale is positioned underneath the slicer such that the slice scale measures an intermediate weight of the draft at a pre-determined point in the slicing process. The intermediate weight information is transferred to the slicer to calculate how many more slices are required at the current slice thickness to achieve the desired weight. The additional weight contributed by the finishing slices is called the completion weight. The completed draft is transferred to the check scale where a final draft weight of the draft is taken. The final draft weight is compared to the sum of the intermediate weight and the completion weight to determine the variance. This variance is then used on subsequent drafts to fine tune the accuracy of the components of the final draft weight.

Numerous other advantages and features of the present invention will become readily apparent from the following detailed description of the invention and the embodiments thereof, from the claims and from the accompanying drawings.

DETAILED DESCRIPTION OF THE PREFERRED EMBODIMENTS

Figure 1:
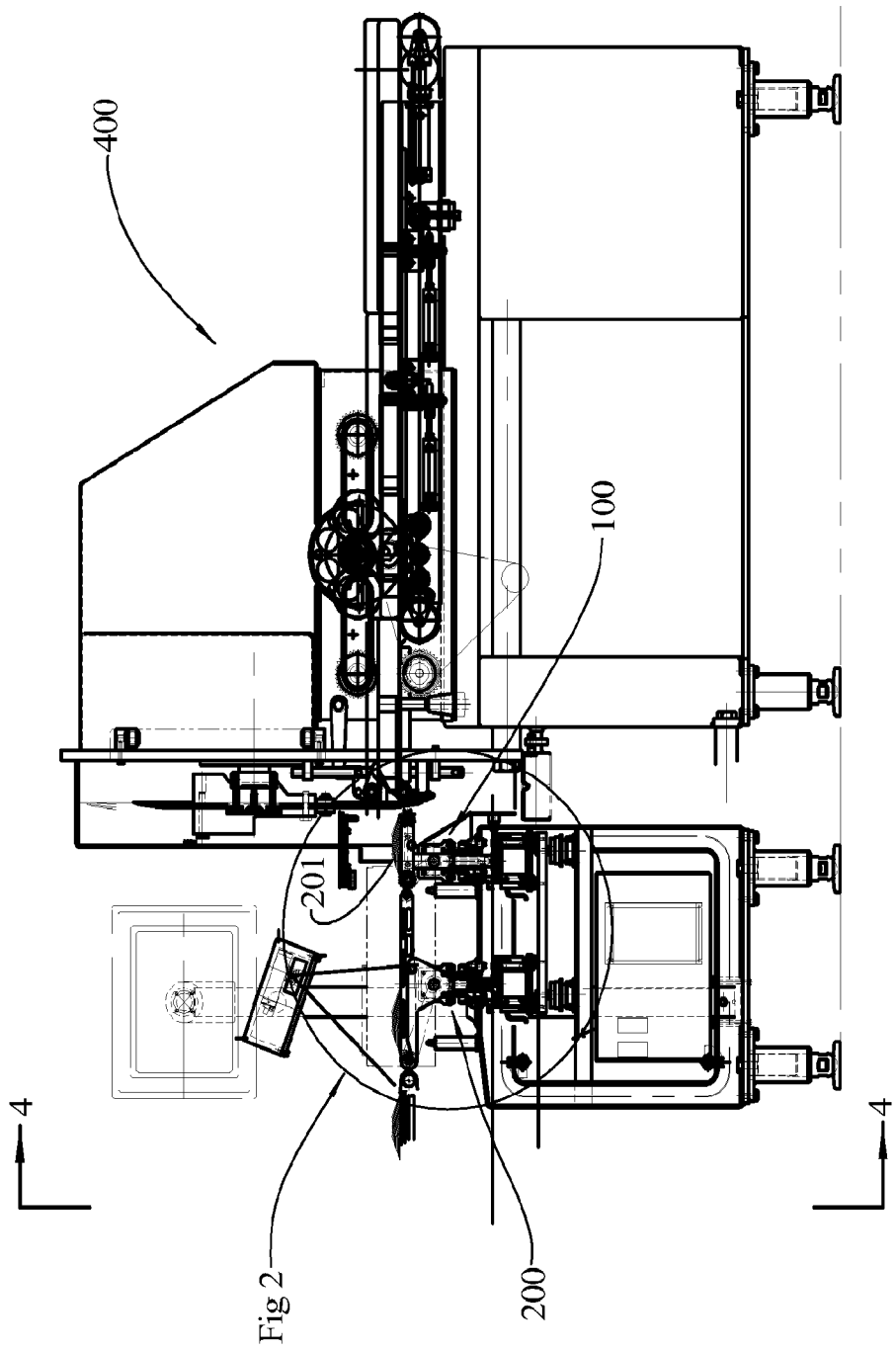
FIG. 1 is a schematic, elevation view, shown partly in cross section, of a dual scale system with a slicing apparatus according to the invention.

While this invention is susceptible of embodiment in many different forms, there are shown in the drawings, and will be described herein in detail, specific embodiments thereof with the understanding that the present disclosure is to be considered as an exemplification of the principles of the invention and is not intended to limit the invention to the specific embodiments illustrated.

Figure 2:
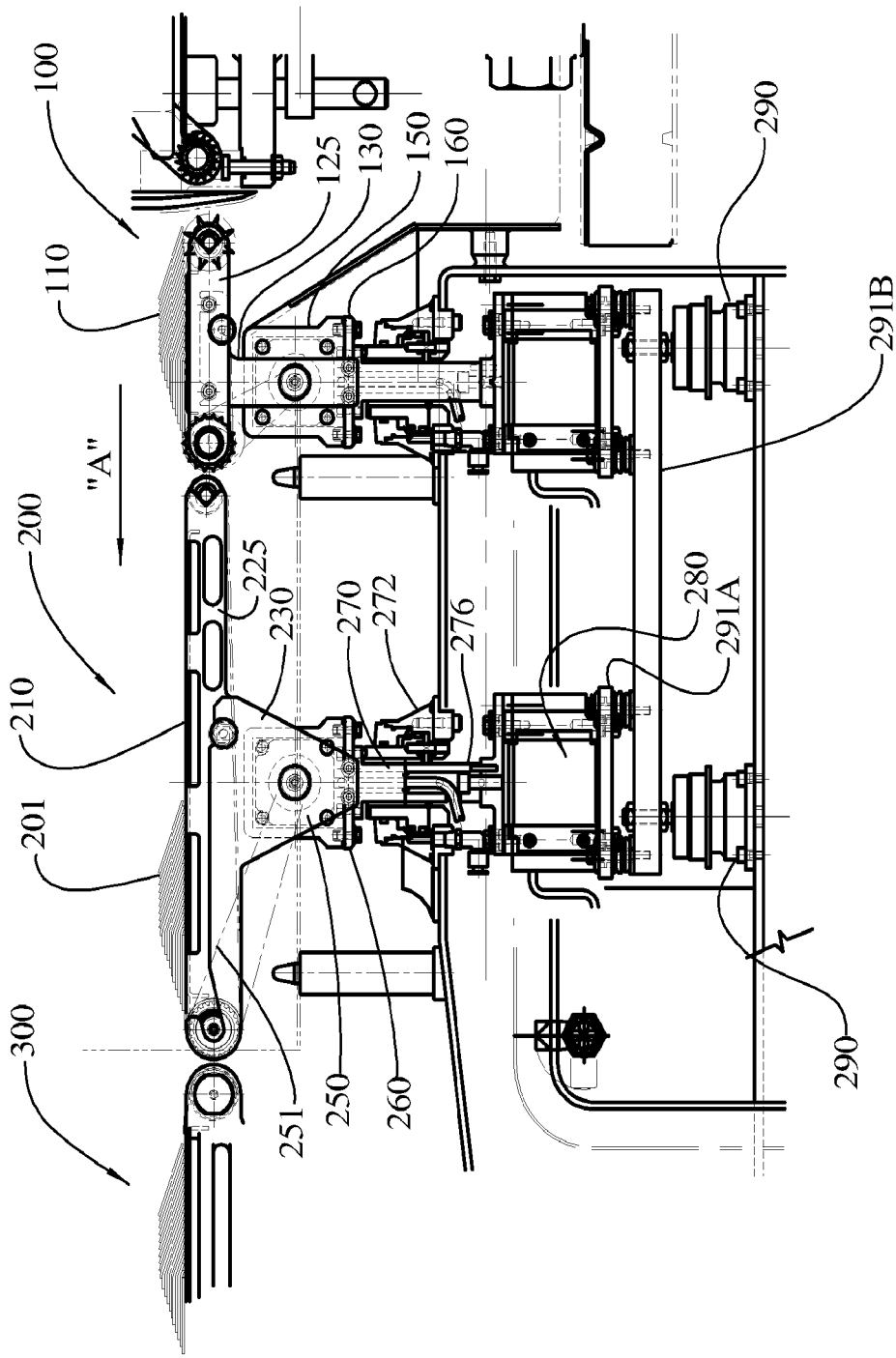
FIG. 2 is an enlarged elevation view, shown partly in cross section, taken from FIG. 1.

FIGS. 1 and 2 illustrate the primary components of the dual scale weighing apparatus. The dual scale weighing apparatus comprises a slice scale 100 and a check scale 200. The slice scale 100 is situated under the discharge end of a slicing machine 400 such that sliced layers of food product or drafts 201, are deposited on the slice scale. The drafts can be straight stacked slices or shingled slices, or any other grouped slices. The check scale 200 is downstream of the slice scale 100, and situated between the slice scale and a downstream conveyor 300.

The slicing machine 400 may be any one of the several different types of slicing machines presently being used in the meat packing industry, for example, the slicer disclosed in U.S. Pat. No. 4,548,108. The slicer is set to slice food products of a certain thickness. Slices are deposited as they are sliced, onto the slice scale 100.

Both the slice scale 100 and check scale 200, as illustrated in FIG. 2, comprise a conveying surface 110, 210, side walls 130, 230, a motor 150, 250, a horizontal plate 160, 260, and a load cell 180, 280. Each component will be further discussed with respect to the check scale 200, but it is to be understood that the slice scale 100 has corresponding components.

Figure 3:
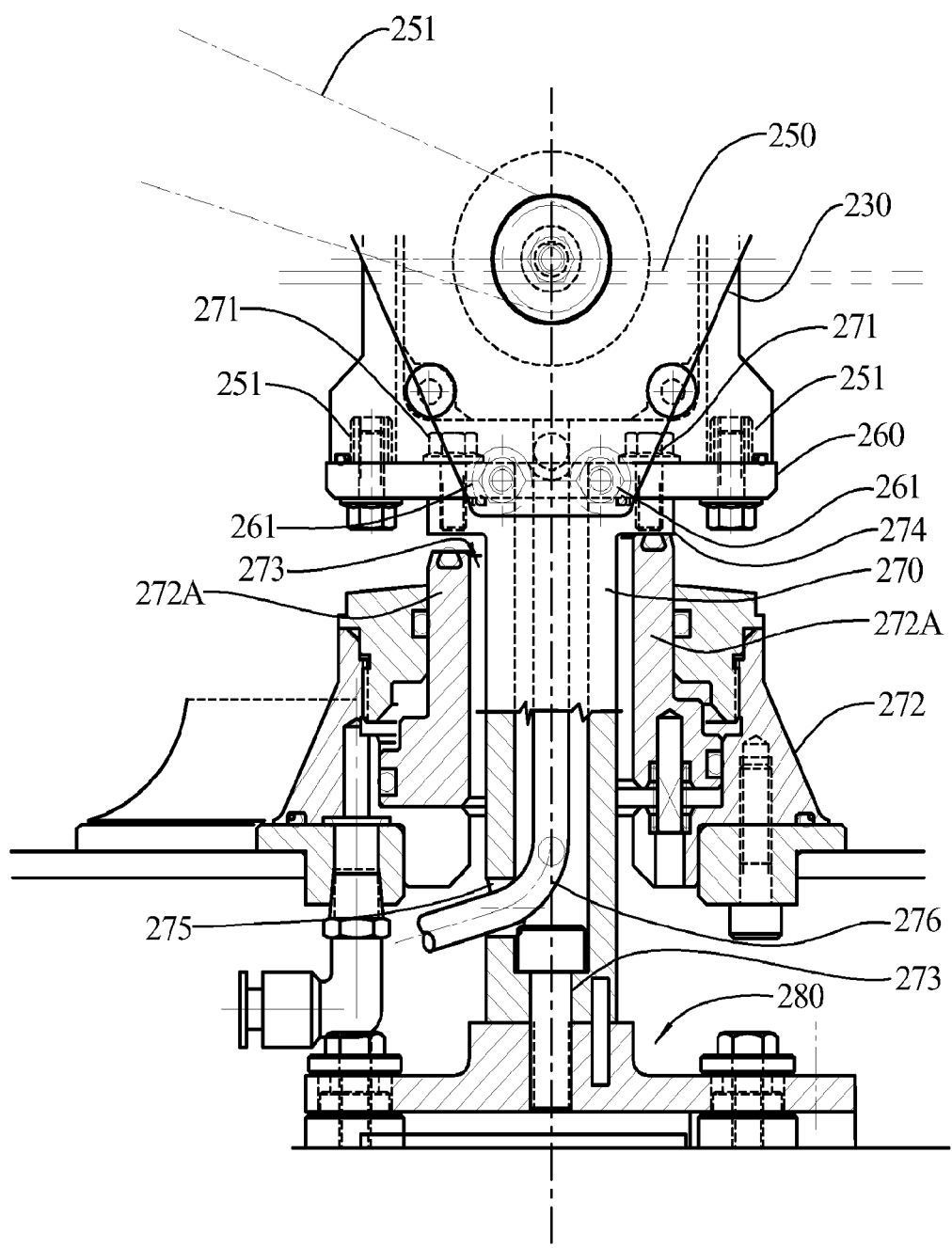
FIG. 3 is an enlarged elevation view, shown partly in cross section, taken from FIG. 2.
Figure 4:
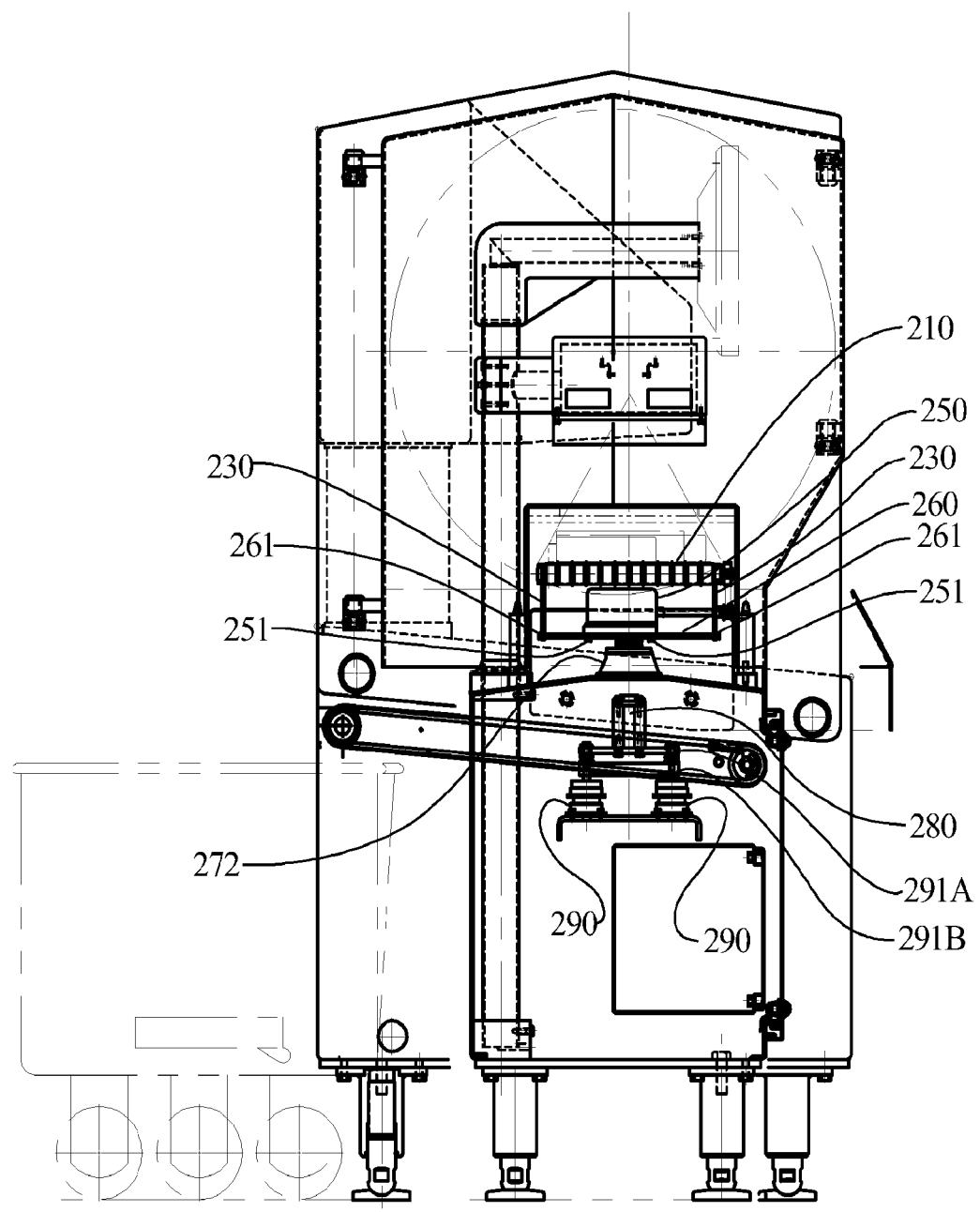
FIG. 4 is a cross sectional view taken generally along line 4-4 of FIG. 1.

The check scale 200 has a conveying surface 210 on which product 201 is conveyed from one end to another, in a direction "A". The conveying surface is driven by a belt 251 coupled to a motor 250, situated beneath the conveying surface 210. The conveying surface is supported by a support frame 225 which is attached to side walls 230 on either side of the support frame (FIGS. 2 and 4). The side walls 230 are attached to a horizontal plate 260 on which the motor 250 rests. The motor is attached to the horizontal plate 260 by screws 251 as illustrated in FIG. 3. The side walls 230 are attached to the horizontal plate 260 by screws 261. The horizontal plate 260, and accordingly the components attached to the horizontal plate 260—the motor 250, side walls 230, and conveying surface 210, is attached to a shaft 270, illustrated in FIGS. 2 and 3. The shaft is housed in a conical shaped housing 272 (FIGS. 2-4). As illustrated in FIG. 3, the top of the shaft contains flanges for screws 271 to attach the horizontal plate 260 to the shaft 270. A fastener 273 is situated at the bottom of the shaft and connects the shaft 270 to the load cells 280 situated beneath the shaft 270. Because the shaft 270 is hollow, an electrical cord 276 providing power to the motor can be run through the shaft to use the shaft as a conduit to prevent wires from being externally exposed. An opening 275 in the shaft near the bottom of the shaft and above the fastener 273 provides an outlet for the electrical cord 276 to exit the shaft 270.

In operation, the weight of the draft 201 is transferred from the conveyer through the side walls 230 to the horizontal plate 260. The weight carried by the horizontal plate is transferred by the shaft 270 to the load cell 280 situated underneath the horizontal plate 260 and the shaft 270. Load cells 180, 280 record weight measurements of the draft. As illustrated in FIGS. 2 and 4, the load cell is attached to a dampening mechanism comprising a load cell plates 291A, dampening plate 291B, and dampeners 290. Each load cell 180, 280 is associated with one scale, and is attached to a load cell plate 291A. The load cell plate 291A is attached to a dampening plate 291 B. The load cell, and load cell plate from each of the check scale and slice scale are attached to the same dampening plate 291 B which sits on top of four vibration dampers 290.

FIG. 3 illustrates that the shaft housing 272 comprises an inner shaft housing 272A which extends above the conical shaft housing 272. The right side flange 274 of the shaft 270 is illustrated as coming in contact with the top of the inner shaft housing 272A, to form a seal. A seal around the top portion of the inner shaft housing 272A is formed when the shaft is lowered to close off the opening of the inner shaft housing 272A, and prevent, for example, debris such as food material or cleaning product from entering the lower portion via the gap 273 between the inner shaft housing 272A and the shaft 270. U.S. Pat. No. 7,411,137 discusses in detail the use of such a sealing arrangement between an upper portion of a weigh scale that is exposed, and a lower portion of the weigh scale that is not intended to be exposed.

The conveying surface can be one continuous surface or a series of belts arranged longitudinally along the direction of travel, as shown in FIG. 1, or other conveying arrangements commonly known to one skilled in the art.

The slice scale 100 is set to weigh the draft at a pre-determined intermediate point in the draft, for example, after 15 slices of a 20-slice draft, or at a pre-determined time period in the slicing process. The weight of the draft taken at the pre-determined intermediate point is the intermediate weight. The intermediate weight information is transferred to the slicer to calculate the minimum number of slices required at a given slice thickness, matching the slice thickness of the current draft, to meet a specified target weight. The calculated number of slices needed to complete the draft is called the completion slices. The weight of the completion slices is called the completion weight.

Without stopping the slicing of the given draft, the slicer completes the draft by slicing out the completion slices. The intermediate weight and the completion weight is added together to arrive at the final estimated draft weight.

The completed draft is transferred by the conveying surface 110 of the slice scale 100 to the check scale 200. The check scale measures the final draft weight of the draft. The final draft weight is compared to the final estimated draft weight to determine the variance. This variance is used on subsequent drafts to fine tune the accuracy of the completion slices to further ensure an accurate final draft weight.

The check scale 200 is located downstream from the slice scale. Like the slice scale, the check scale comprises a conveying surface 210 with a weigh scale situated beneath the conveying surface. The conveying surface 210 is made from a flexible, thin, and preferably lightweight material such that the weight of the sliced product can be accurately transferred to the scale and reflected in the weight measured.

Once the draft has been weighed on the check scale 200 and weight information has been collected and transferred for further calculations, the draft is moved downstream to a processing conveyor 300 which transports the draft for further processing such as packaging. All the conveyors disclosed in the present invention can be driven by a belt coupled to a motor or by other means known to those skilled in the art.

The weight information from the slice scale is transferred directly to a data management system such as the control of the slicer, or transferred to an external data managing and controlling system, such as a computer, for further processing. The computer calculates the completion weight and the number of completion slices needed, and determines the final estimated draft weight. Weight information from the check scale 200 is also transferred to the computer to compare the final estimated draft weight with the final draft weight.

In other embodiments, it is possible to have multiple streams of conveying surfaces such that multiple drafts are processed simultaneously using the present invention. In other embodiments, several weight scales can be positioned under a widened conveying surface to accommodate the weighing of multiple drafts simultaneously.

In some embodiments, intermediate weight information can be obtained at more than one pre-determined intermediate point. Having several pre-determined intermediate points allows more frequent fine tuning of the remaining slices leading up to, and including the completion slices. Having more than one pre-determined intermediate point is particularly useful for food products with high cross sectional variation due to size irregularities or lack of uniformity of composition.

In some embodiments, the dual scale apparatus is used in conjunction with a tare correction system. The tare correction system can automatically zero the scale once a pre-determined number of drafts have been processed, or even after each draft. A tare correction system is particularly useful in conjunction with food products that often leave scraps or liquids, or other buildup on the scales. The tare system can be set to reset the scale immediately after each draft has been conveyed to the check scale and before the first slice of the next draft has been deposited, so as not to interfere with continuous slicing.

In other embodiments, intermediate weight information can be transferred to the slicer to control and change slice thickness. While it is generally preferable to have slices of uniform appearance from a consumer standpoint, minor changes, such as changes in thickness may not be detectable by the consumer and can assist in minimizing the give away weight of the sliced product. Changing slice thickness is preferably done with drafts comprising a higher number of slices and wherein the pre-determined intermediate point in the draft is early on in the draft, so as to allow any adjustments needed to reach the completion weight to be spread out over a higher number of slices in order to minimize significant changes in slice thickness. Using intermediate weight information to generate a change in thickness in addition to calculating slices needed to fulfill the completion weight will minimize the give away weight, as it would be possible to exactly aim for the target weight, as opposed to rounding up to the nearest whole integer the number of slices required to meet the target weight.

From the foregoing, it will be observed that numerous variations and modifications may be effected without departing from the spirit and scope of the invention. It is to be understood that no limitation with respect to the specific apparatus illustrated herein is intended or should be inferred.

All references, including publications, patent applications, and patents, cited herein are hereby incorporated by reference to the same extent as if each reference were individually and specifically indicated to be incorporated by reference and were set forth in its entirety herein.

The invention claimed is:

1. A method of producing drafts of sliced products with desired weights, the drafts being conveyed along a food processing line downstream of a slicer, comprising the steps of:
    slicing food product slices directly onto a slice scale positioned underneath the discharge end of the slicer to form drafts of sliced products;
    measuring an intermediate weight of the draft using the slice scale, at a pre-determined point while a slicing process is in progress;
    transferring the intermediate weight measurement to a data managing system to calculate a completion weight; and
    slicing at least one completion slice onto the draft of the sliced product without interruption of the slicing process, the at least one completion slice weighing an amount equal to the completion weight within a predetermined tolerance so as to produce a completed draft, wherein a weight of the completed draft is within a desired weight so as to eliminate rejection of the completed draft so that no addition or subtraction of the sliced product occurs after the draft is completed;
    measuring the weight of the completed draft to determine a final draft weight and comparing the final draft weight to the sum of the intermediate weight and the completion weight; and
    wherein slicing the at least one completion slice and slicing of the food product slices occurring during a single process while the slices are on the slice scale positioned underneath the discharge end of the slicer.

2. The method of claim 1, wherein the step of measuring the weight of the completed draft comprises transferring the completed draft from the slicing scale to a check scale for weighing.

3. The method of claim 2, wherein the step of transferring the completed draft to a check scale comprises moving the draft along a conveying surface on the slice scale towards the check scale.

4. The method of claim 1, wherein the step of comparing the final draft weight to the sum of the intermediate weight and the completion weight comprises calculating a variance between the final draft weight and the sum of the intermediate weight and the completion weight.

5. The method of claim 4, further comprising the step of adjusting the slicing of a subsequent draft using the calculated variance so as to fine tune a slice thickness.

6. The method of claim 1, wherein the step of slicing the at least one completion slice comprises calculating the minimum number of slices needed at a given slice thickness to meet the completion weight.

7. The method of claim 1, wherein the step of calculating a completion weight comprises the step of subtracting the intermediate weight from the desired weight.

8. The method of claim 1, wherein the step of measuring the intermediate weight is done without stopping the slicer.

9. The method of claim 1, wherein more than one intermediate weight is measured.

10. The method of claim 1, wherein the step of slicing the at least one completion slice comprises slicing slices wherein at least one slice is of a different thickness than other slices in the completed draft.

11. A weighing system for producing drafts of desired weights, the drafts being sliced by a slicer and conveyed along a food processing line downstream from the slicer, the system comprising:
    a slice scale with a conveying surface, the slice scale disposed beneath the discharge end of the slicer, the slicer configured to directly deposit food product slices on the slice scale;
    the slice scale configured to determine a weight of an intermediate draft;
    a data management system in signal communication with the slice scale and the slicer, and configured to receive the intermediate weight from the slicer, and calculate a completion weight, while a slicing process is in progress;

the data management system configured to control the slicer to produce at least one completion slice, the at least one completion slice weighing an amount equal to the completion weight within a predetermined tolerance to produce a completed draft, wherein a weight of the completed draft is within a desired weight so as to eliminate rejection of the completed draft so that no addition or subtraction of the sliced product occurs after the draft is completed; and wherein the weight of the completed draft is measured to determine a final draft weight and the final draft weight is compared to the sum of the intermediate weight and the completion weight.

* * * * *